(12) United States Patent
Shelemay et al.

(10) Patent No.: US 7,090,494 B2
(45) Date of Patent: Aug. 15, 2006

(54) IMPLANT FOR USE IN AESTHETIC REGIONS OF THE MOUTH WITH COLORED CONTOURED EDGE PORTION

(75) Inventors: Avi Shelemay, Toronto (CA); Mike Kehoe, Mississauga (CA)

(73) Assignee: Innova Corp., Toronto (CA)

( * ) Notice: Subject to any disclaimer, the term of this patent is extended or adjusted under 35 U.S.C. 154(b) by 412 days.

(21) Appl. No.: 10/752,702

(22) Filed: Jan. 8, 2004

(65) Prior Publication Data

US 2004/0191727 A1 Sep. 30, 2004

Related U.S. Application Data

(63) Continuation-in-part of application No. PCT/CA02/01055, filed on Jul. 10, 2002.

(30) Foreign Application Priority Data

Jul. 12, 2001 (CA) .................................... 2353051

(51) Int. Cl.
*A61C 8/00* (2006.01)
(52) U.S. Cl. ....................... 433/173; 433/175
(58) Field of Classification Search ................ 433/173, 433/172, 223, 175, 176, 191, 192, 193, 194
See application file for complete search history.

(56) References Cited

U.S. PATENT DOCUMENTS

| 4,671,768 A | 6/1987 | Ton |
| 5,344,457 A | 9/1994 | Pilliar et al. |
| 6,095,817 A | 8/2000 | Wagner et al. |
| 6,174,167 B1 | 1/2001 | Wohrle |
| 6,854,972 B1 | 2/2005 | Elian |

FOREIGN PATENT DOCUMENTS

WO    WO 01/49199 A2    7/2001

*Primary Examiner*—Cary E. O'Connor
*Assistant Examiner*—Candice C. Stokes

(57) ABSTRACT

An implant includes an implantable body portion adapted to be at least partially recessed within a patient's alveolar bone, and which has a peripheral surface portion, which is configured to stimulate and/or facilitate the engagement of osteoblasts and other bone tissues with the implant. The implant body provides bone engaging regions along one or more of the distal and/or mesial implant surfaces, which are elongated relative to bone engaging regions on the lingual and/or buccal surfaces of the implant body. In particular, the implantable portion of the implant body includes a bone engaging surface which, when the implant body is fully seated within the patient's jaw bone, extends from a distal portion of the implant body to a remote proximal-most edge. The proximal-most edge has a contour selected to generally follow a predetermined crestal outline of the supporting bone tissue.

23 Claims, 5 Drawing Sheets

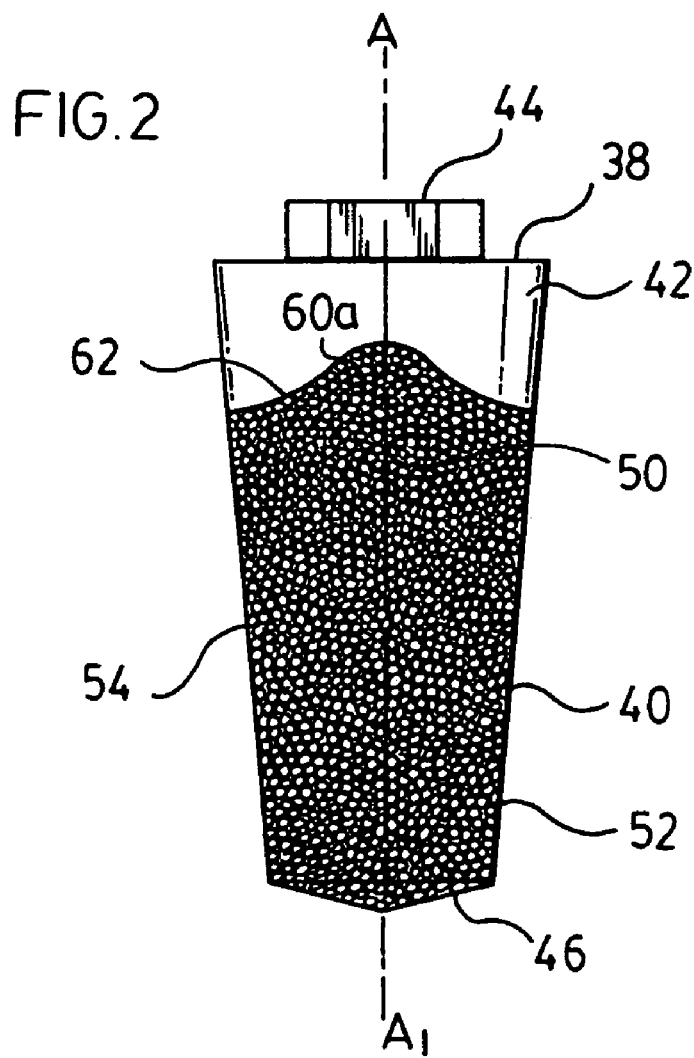
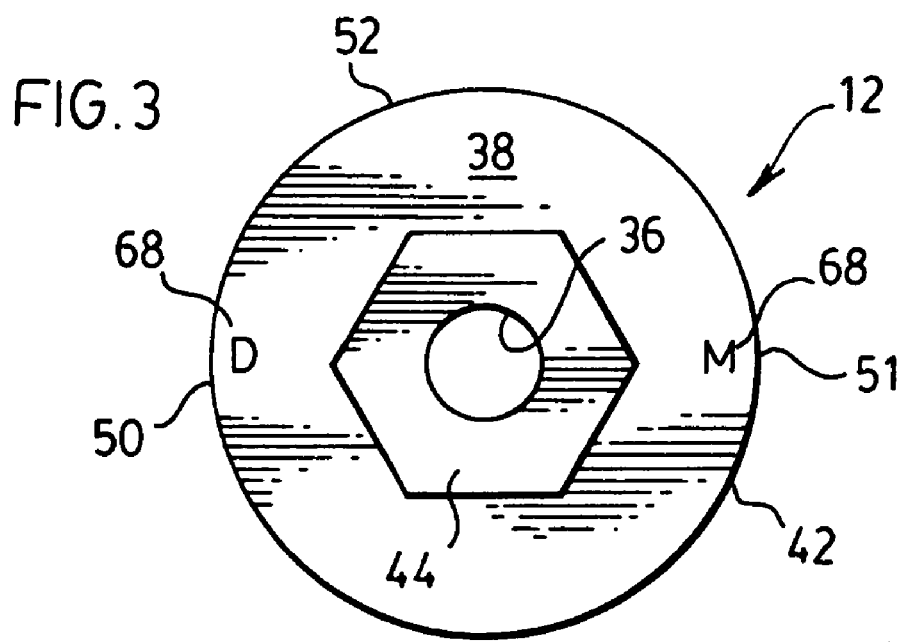

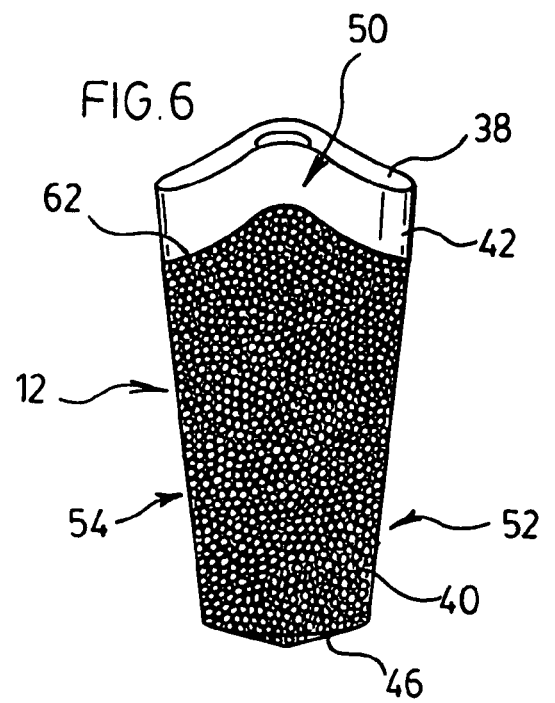
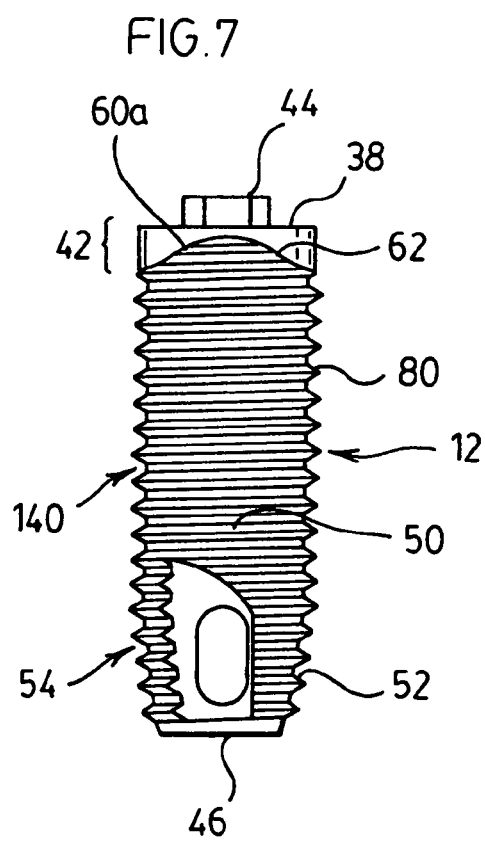
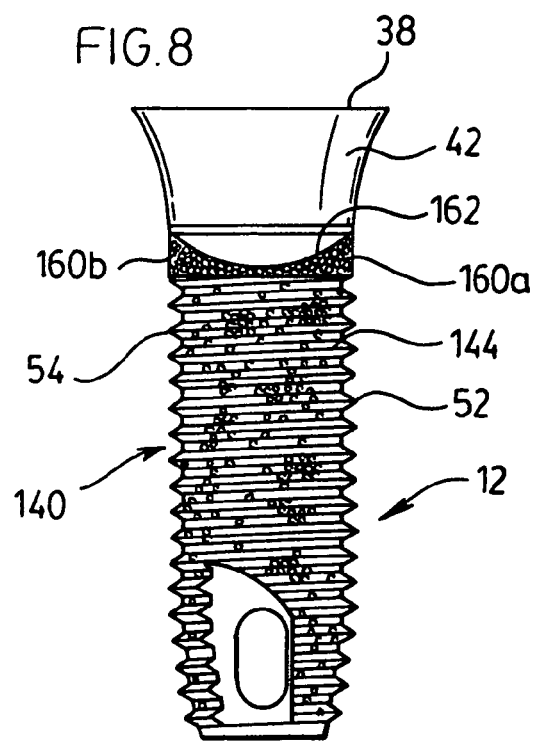

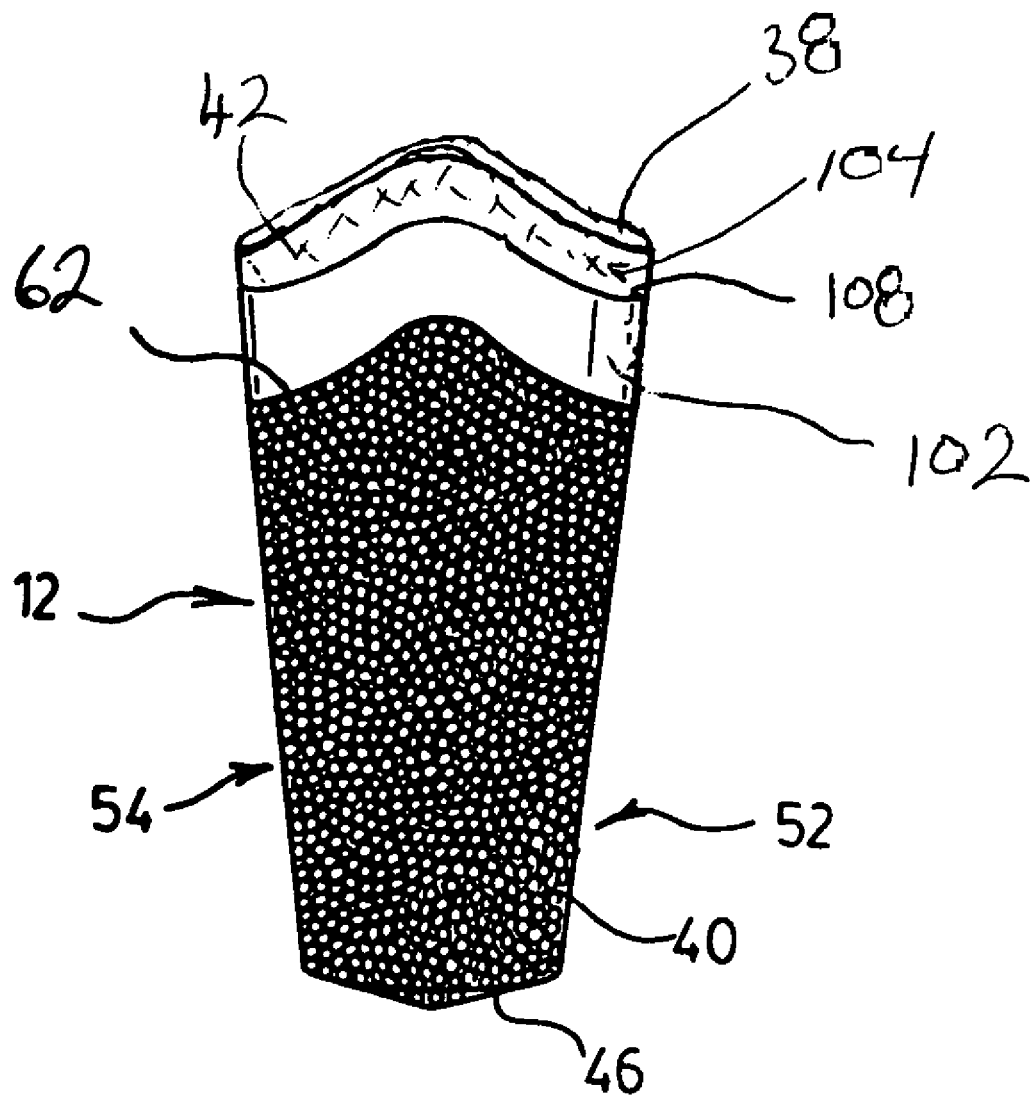

IMPLANT FOR USE IN AESTHETIC REGIONS OF THE MOUTH WITH COLORED CONTOURED EDGE PORTION

RELATED APPLICATIONS

This application is a continuation-in-part of International application serial No. PCT/CA02/01055, with an international filing date of Jul. 10, 2002, and entitled "Implant For Use In Aesthetic Regions Of The Mouth".

SCOPE OF THE INVENTION

The present invention relates to a dental implant to be used in areas in the mouth where aesthetics are of a high concern, and more preferably an implant which has a bone engaging coated, textured and/or porous portion which has a contour selected to approximately mirror a predetermined surface contour of bone tissues at the site of implant placement, and an upper coronal band portion which has a colour selected to complementarily blend with the colouring of the patient's gum tissue.

BACKGROUND OF THE INVENTION

Conventional implant constructions are generally of a two-part design and include a body portion which is adapted to be recessed into the patient's jaw, and a prosthesis in the form of a ceramic tooth which is adapted for coupling to a proximal end of the body. The implantable body which is made from stainless steel, titanium or other suitable metals or alloys is configured to be recessed into a suitable bore hole formed in the patient's jaw bone at the site of a lost tooth. Typically, the body has a threaded interior or is otherwise configured to mechanically receive thereto an attachment post which serves as a support for the ceramic tooth.

U.S. Pat. No. 5,344,457 to Pilliar et al., entitled "Porous Surfaced Implant", discloses a frustoconical shaped implant which is characterized by a porous coated bone engaging lower portion and a smooth non-porous upper bone attachment region or collar. The implant is press-fitted into a complementary sized bore formed in the patient's jaw bone at the site of placement and over time, bone tissues grow into and engage the porous coating on the lower portion of the implant to firmly anchor it in the place of a natural tooth. The implant which is the subject of U.S. Pat. No. 5,344,457 has achieved a significant degree of success in the market place, and is presently sold by Innova Corp. of Toronto, Canada, under the name Endopore®. Endopore® dental implants are used in the replacement of various teeth including, lost molars and bicuspid teeth in the anterior and posterior regions of the mouth.

Other conventional implant constructions are characterized by the implantable body being cylindrical in shape and provided with a roughened lower exterior surface, texture, external thread configuration and/or coating, to facilitate the engagement of the implant body with the patient's surrounding bone tissues and its anchoring in place.

A difficultly exists with conventional implants in that todate, they have achieved limited success in replacing incisors and teeth in the frontal-most regions of the mouth where high aesthetic demands exist. The abutment-implant interface, also termed "microgap", is believed to harbor bacteria and bacterial products following exposure to the oral environment. This in turn results in the establishment of a "biological width" around the implant (i.e. the distance from the peri-implant bone crest to the microgap). The biological width is relatively constant and seems to be approximately 2 mm, similar to the biological width present around natural teeth. It has been found that following implantation, crestal bone remodeling occurs, whereby supporting bone tissues and the overlying bone tissues tend to recede to the uppermost peripheral edge of the textured or porous coated bone engaging portion of the implant body. A further variable that can play a role in crestal bone remodeling is lack of mechanical coupling around any smooth upper collar surface. For example, it has been demonstrated that the crestal bone resorption around Endopore® implants stops at the junction of the smooth collar and the porous surface. It has been suggested that the lack of mechanical coupling around the smooth collar surface results in "disuse atrophy" of the crestal bone to the level of the junction with the porous surface. This has been demonstrated also with other textured implant surfaces.

The receding supporting tissues or crestal bone loss around dental implants has led to an aesthetic challenge when attempting dental restorations in that it may result in exposure of the metal implant body, greatly detracting from the natural appearance of the prosthesis. Conventional implants suffer the disadvantage in that the alveolar bone which encases the tooth root tends to gradually disappear along the portion of the implant where engagement of bone tissue with the implant body does not occur. This leads to a corresponding recession of the sulcus and overlying gum tissues which gradually results in the exposure of the silver/grey stainless or titanium steel body of the implant. In the more aesthetically important regions of the mouth, the exposure of the stainless steel portion of the implant body may be seen through the patient's gum tissue as a grey tinted band, greatly detracting from the natural look of the prosthesis.

This problem is particularly pronounced in the anterior regions of the mouth and when using two implants positioned adjacent to each other. Loss of inter-implant bone height (as a result of the normal crestal bone remodeling that is associated with each of the implants) results in the absence of a papilla between the two implants due to lack of bone support. This creates an aesthetic deformity, often termed "black triangle", between the two implant crowns. "Black triangles" are particularly visible when present in the maxillary anterior region and the patient has a high lip line. The patient's perception of a successful implant-supported prosthesis depends not only on restoring function, but also on restoring normal anatomy and aesthetics. The lack of a papilla and the presence of a "black triangle" can lead to patients' dissatisfaction with the whole implant treatment, even with patients having a low smile line. Heretofore, the dental profession has been forced to come up with techniques to deal with "black triangles". Most commonly, pink acrylic or porcelain is added to the final restoration to replace the missing papilla. This solution is far from ideal since it is impossible to replicate the gingival tissue with acrylic or porcelain in terms of texture and colour. Several attempts have also been made in establishing surgical procedures that will regenerate the missing papilla; however, these procedures are very unpredictable and seldom result in 100% regeneration.

Conventional implants are poorly suited to accommodate for the crestal bone remodeling which occurs with implants. With conventional implant designs, most often any bone engaging textured, porous or coated surface extends downwardly from an uppermost radial edge surface which is located a constant distance from the lower apex of the body.

Conventional implant designs suffer the disadvantage that they fail to account for the fact that with natural incisor teeth, the surface contour of healthy supporting bone tissues tends to be higher along the distal and medial surfaces of the tooth than along the lingual and buccal regions. Heretofore, the bone engaging regions for conventional implants have either been limited by the lowermost extent of expected bone recovery, weakening the integrity of the dental implant attachment, or suffer the disadvantage that the lingual and buccal portions of the implantable portion of the implant body may be visible at the patient's gum line.

SUMMARY OF THE INVENTION

To at least partially overcome the disadvantages of the prior art, the present invention seeks to provide an implant which includes an implantable body portion adapted to be at least partially recessed within a patient's alveolar bone, and which has a peripheral surface portion which is configured to stimulate and/or facilitate the engagement of bone tissues with the implant.

In a healthy jaw, the root of the tooth is supported by alveolar bone, with lamellated bone surrounding the root of the tooth where periodontal ligament fibres attach. The shape and crestal outline of interdental bone will to a large extent depend upon the shape and size of the tooth roots, with the distance from the crest of the alveolar bone to the cementoenamel junction of the tooth in a healthy periodontium being about 2 mm and a healthy sulcus extending about 0.5 mm. The present implant construction preferably seeks to stimulate osteoblasts, namely the bone forming cells, so as to promote bone ingrowth into and otherwise engage the implantable portion of the implant, with the crestal surface of the regrown bone tissues substantially mirroring that of a healthy tooth, to firmly anchor the implant in place.

Another object of the invention is to provide an improved dental implant body for use in the anterior regions of the mouth, and which provides bone engaging regions along one or more of the distal and/or mesial implant surfaces which are elongated relative to bone engaging regions on the lingual and/or buccal surfaces of the implant body.

Another object of the invention is to provide an implant body configuration which is configured to stimulate crestal bone tissue remodeling to a normal pre-implant height.

Another object of the invention is to provide a dental implant body which has a bone engaging porous, textured, threaded and/or coated exterior surface, which is applied to the peripheral surface of the implant body in a configuration which reflects the actual or a preselected optimum contour of the crest of the alveolar bone and/or lamellated bone tissues at the site of implant placement.

The implantable portion of the implant body could for example include about all or only part of its periphery, a bone engaging surface which, when the implant body is fully seated within the patient's jaw bone, extends from a distal portion of the implant body to a remote proximal-most edge. The proximal-most edge has a contour selected to generally follow a predetermined crestal outline of the supporting bone tissue. The bone engaging surface could take a number of possible forms including without restriction: an externally threaded portion, in which the proximal-most thread patterns are configured to generally follow the surface contour of alveolar and/or lamellated bone; an acid etched, physically abraded or other roughened or textured peripheral surface of the implant body; a porous coated surface which, for example, could consist of titanium, metal or ceramic beads and/or a chemically coated portion. Suitable chemical coatings for use with the bone engaging surface would typically comprise bioreactive coatings, including coatings formed from hydroxyapatite and other compounds suitable for stimulating bone tissue growth, and which facilitate the anchoring of the implant body by bone tissues following its placement.

The predetermined crestal outline could by way of non-limiting example, be selected as a crestal outline of the patient's own alveolar and/or lamellated bone tissues at the site of implant placement or at the site of one or more of the patient's own teeth, or the crestal outline of alveolar and/or lamellated bone tissues of a typical healthy jaw, and more preferably the crestal outline at the site of or proximate to the intended site of implant placement.

The bone engaging portion of the implant body could, for example, consist of a narrow band between the proximal exposed end of the implant body, and the distalmost end tip of the implant which is recessed into the patient's jaw. The bone engaging portion may further extend partially or completely about the circumference of the implant body. More preferably, however, the bone engaging region extends from approximately adjacent to the distalmost apex of the implant body to a proximal edge surface which, following placement of the implant body, approximately coincides with the crest of the alveolar bone of either the patient's missing tooth or a healthy tooth.

In one aspect, the "aesthetic implant" design features of the present invention are therefore based on the principles governing peri-implant crestal bone loss, and aim at maintaining the interproximal bone at a level that is coronal to the buccal and lingual bone levels. In one simplified construction, the implant is designed to be inserted in a single stage surgery, thereby ensuring adequate biological width between the microgap and the crest of the bone.

Although not essential, the implant body could be generally frustoconical in shape and, for example, be provided with a porous coated and/or textured bone engaging exterior surface which is designed to be "press-fit" in a specific buccal/lingual and mesial/distal orientation. In such an embodiment, the invention is directed to an improved dental implant which is suitable for use in aesthetic regions of the mouth, including as replacement for upper incisor teeth, and may be developed as a modification of the Endopore® implant disclosed in U.S. Pat. No. 5,344,457. The implantable portion of the implant may optionally be provided with a smooth upper collar portion which, for example, is provided to prevent or minimize the accumulation of oral bacteria. The smooth collar portion could, in a first embodiment, be provided as a smooth band which extends from the proximal edge of the bone engaging surface to a proximal end of the implant body which is provided with a substantially constant width, extending from the bone engaging surface to a contoured implant end surface which also follows the general contour of the crestal surface of the alveolar bone. In an alternate embodiment, the smooth collar of the implant body could extend from the proximal-most edge of the lower bone engaging portion to a generally flat proximal implant body surface.

In another construction, the present invention seeks to provide an improved cylindrical implant body which is characterized by a bone engaging portion which, by way of non-limiting example, could comprised helical threads, ribs and/or a roughened implant surface formed by grit blasting and/or acid etching. The bone engaging portion most preferably extends from a lowermost distal end of the implant to a contoured upper edge which at least generally follows the contour of the patient's crestal bone or a pre-selected typical contour of healthy bone tissue at the site where the implant is to be used.

A further construction of the invention provides an improved implant coating which is selected to provide enhanced engagement between the bone tissue and the implant body, and which for example could comprise a hydroxyapatite or other dentally active coating used to facilitate the anchoring of the implant in situ in a patient's jaw. The dentally active coating is applied about at least part of the circumference of the implant body, and depending upon the intended site of implant placement, extends from a distalmost end portion of the implant body to a proximalmost edge. The coating is applied so as to be elongated along one or more of the lingual, distal mesial and/or buccal sides of the implant body. More preferably, the coating is applied such that its proximal edge of the coating generally mirrors the typical crestal surface contour of either the patient's own or healthy bone tissues at the site at which the implant is to be used.

It is envisioned that the dental implant could also be placed in the patient's alveolar bone in two stages. During the first stage surgery, the implant body is submerged into a complementary size bone formed in the bone to the level of a proximal end cap or platform used as a temporary cover over the proximal end of the implant. Following initial placement, a period of time is provided to allow bone tissue regrowth so as to grow into and engage the bone engaging surface and firmly anchor the implant body in place. As a next stage the proximal end platform is removed, and an abutment and suitable prosthesis are then coupled to the proximal end of the implant body in a mechanical and/or chemically bonded fit arrangement.

Accordingly, in one aspect the present invention resides in a dental implant for use in replacing a missing tooth in a patient's jaw bone comprising, an implant body adapted to be at least partially recessed into a portion of said patient's jaw bone, said implant body extending longitudinally along an axis from a distalmost apex to a proximal end portion, a coloured coronal band portion provided about a peripheral surface of said implant body adjacent said proximal end portion, said coloured portion having a colour which is complementary to a natural gum tissue colour of said patient so as not to significantly discolour the gum tissue if seen therethrough, a bone engaging surface provided about at least a portion of said peripheral surface of said implant body, and being spaced from said coloured band portion towards said apex said bone engaging surface selected to promote bone tissue ingrowth or attachment thereto and extending longitudinally along said periphery of said implant body to a proximal edge spaced towards said proximal end portion, wherein at least a portion of said proximal edge having a contour selected to generally follow a crestal surface contour of preselected bone tissues.

In another aspect, the present invention resides in a dental implant for use in replacing a missing tooth in a patient's jaw bone comprising, an implant body portion adapted to be recessed into a portion of said patient's jaw bone, said implant body extending longitudinally along an axis from a distalmost apex to a proximal end portion, a coloured coronal band portion provided about said implant body portion immediately adjacent said proximal end portion, said coloured band portion comprising a gold coloured plating or coating and extending axially between 0.5 to 2.5 mm along said implant body.

a bone engaging surface spaced distally from said coloured band coating towards said apex and providing a peripheral surface of said implant body, said bone engaging surface selected to promote bone tissue ingrowth or attachment thereto and extending longitudinally along said periphery of said implant body to a proximal edge spaced towards said proximal end portion, wherein the proximal edge of the bone engaging surface has a contour selected to generally follow a crestal surface contour of a pre-selected jaw bone adjacent said missing tooth.

In a further aspect, the present invention resides in a dental implant for use in replacing a natural tooth in a patient's jaw bone comprising, an implant body extending longitudinally along an axis from a lowermost apex to an upper end portion and including, an uppermost coloured coronal band surface adjacent to said upper end portion and providing a first peripheral surface portion of said implant body, said coloured band portion comprising a substantially smooth portion having applied thereto a coating selected from a group consisting of a gold-coloured titanium nitride coating, a yellow gold coating, a yellow gold alloy coating, a pink gold coating and a pink gold alloy coating, a bone engaging surface providing a second peripheral surface portion of said implant body adapted to be recessed into said patient's jaw bone, said bone engaging surface selected to promote bone tissue ingrowth or attachment thereto and extending longitudinally along said periphery of said implant body substantially from said apex to an upper edge spaced towards said upper end portion, wherein the upper edge of the bone engaging surface has a contour selected to generally follow a crestal surface contour of healthy bone tissues at a site of implant placement, and a textured peripheral portion intermediate said bone engaging surface and said coloured band portion, the textured peripheral portion selected from a laser abraded portion, an acid etched portion, and mechanically abraded portion, and an abutment for supporting a prosthesis thereon.

BRIEF DESCRIPTION OF THE DRAWING

Reference may be now had to the accompanying detailed description, together with the accompanying drawing pages in which:

FIG. 2 shows an enlarged schematic side view of the distal surface of the implant body used in the implant construction of FIG. 1;

FIG. 3 shows an enlarged plan view of the proximal end of the implant body shown in FIG. 2;

FIG. 6 shows a schematic side view of a distal/mesial side of an implant body in accordance with a second embodiment of the invention;

FIG. 7 illustrates a schematic view of a distal/mesial side of an implant body in accordance with a third embodiment of the invention;

FIG. 8 illustrates a schematic view of a distal/mesial side of an implant body construction in accordance with a fourth embodiment of the invention; and FIG. 9 illustrates schematically a side view of a distal/mesial side of an implant body in accordance with a further embodiment of the invention.

DETAILED DESCRIPTION OF THE PREFERRED EMBODIMENTS

Figure 1:
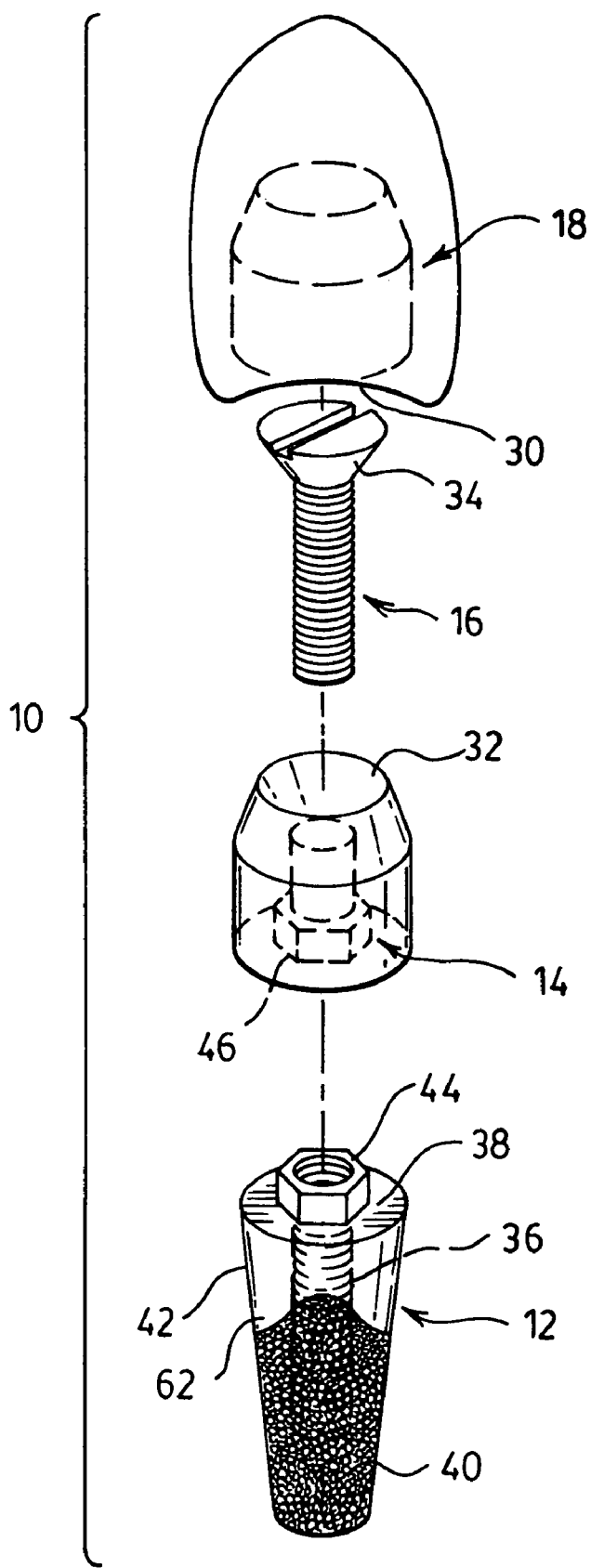
FIG. 1 illustrates an exploded view of a dental implant construction in accordance with a first embodiment of the invention.

FIG. 1 illustrates an exploded implant construction 10 used in the replacement of a lost anterior or maxillary tooth, in accordance with a first preferred embodiment of the invention. The implant construction 10 consists of an implantable titanium or stainless steel body 12, a stainless steel abutment assembly 14, a stainless steel retaining screw 16, and a ceramic tooth prosthesis 18 which has a profile and size selected to mimic the patient's natural tooth which is to be replaced. As will be described, the implant construction 10 is adapted to be recessed at the site of a missing anterior or maxillary tooth within the lamellated and alveolar bone tissues 20,22 of the patient's jaw 24 (FIG. 4) in the place of the lost natural tooth.

The abutment assembly 14 serves as the base support for the prosthesis 18 and has an exterior shape selected for fitted engagement within a complementary sized recess 30 formed in the bottom of the prosthesis 18. A central bore 32 is formed through the center of the abutment 14 which is sized to receive therein the screw 16 while preventing the screw head 34 from moving therethrough. It is to be appreciated that although FIG. 1 illustrates a one-part abutment assembly 14, its individual abutment components and configuration may vary having regard to the configuration of the prosthesis 18. In the final assembly of the implant construction 10, the prosthesis 18 is secured in place over the abutment assembly 14 by a suitable dental cement.

As shown best in FIG. 1, the implantable body 12 is formed with an internally threaded axial bore 36 which extends downwardly from a proximal surface 38 of the implant body to which the abutment assembly 14 is mounted approximately three-quarters along its longitudinal length. The internal threads of the bore 36 are selected for threaded engagement with the retaining screw 16, to enable the mechanical coupling of the assembly 14 to the implant body by means of the retaining screw 16. As will be described, following the positioning of the body 12 in a complementary sized bore formed in the patient's jaw 24, the abutment assembly 14 is coupled to the implant body 12 by inserting the screw through the bore 32 and into threaded engagement with the internal treads of the bore 36.

FIG. 2 shows best the implant body 12 construction in accordance with the first embodiment of the invention where the implant body 12 is configured for use with a conventional abutment 14 and prosthesis 18, as for example is shown in FIG. 1. Although not essential, the implant body 12 most preferably has a tapered frustoconical shape. The body 12 has two principle portions or surfaces, namely a distalmost porous coated surface 40 for primary fixation of the implant (i.e. bone-engagement) with the patient's bone tissues, as well as a non-porous smooth upper or coronal surface 42. The coronal surface 42 is provided to prompt the maintenance of bone surrounding the surface of the implant 10. As shown best in FIGS. 2 and 3, a hexagonal mount 44 projects upwardly from the proximal end surface 38 of the implant body 12. The hexagonal mount 44 is centered on the elongated central axis A–A$_1$ (FIG. 2) of the implant body. As seen best in FIG. 3, the central bore 36 extends downwardly through the center of the hexagonal mount 44 in the axial direction. The hexagonal mount 44 more preferably has a size and shape selected for fitted placement within a complementary sized recess 46 (FIG. 1) which is formed in the bottom of the abutment assembly. FIG. 2 further shows best the proximal end surface 38 as comprising a substantially flat surface extending radially generally normal to the axis A–A$_1$.

The implant body 12 is shown as frustoconically shaped along its entire length, however, the invention is not so limited and other implant configurations which taper only partially along their axial length are also possible. Preferably, the implant body 12 tapers inwardly from the proximal end surface 38 to a distalmost apex 46, which, as seen best in FIG. 4, orients in a downwardmost position in a complementary bore 48 formed in the patient's jaw 24 at the site of implant placement. The implant body 12 tapers toward the distalmost apex 46 at an angle of between about 1 and 20 degrees, preferably 2 and 10 degrees, and still more preferably at approximately 3 to 5 degrees.

FIG. 2 shows the distal side face 50 of the implant oriented in a forwardmost direction, with the mesial side face 51 (FIG. 3) having substantially the mirror construction, and the lingual and buccal implant side faces identified by reference numerals 52 and 54, respectively. As seen best in FIG. 2, the non-porous coronal surface 42 of the implant body 12 adjacent to the end surface 38 is provided with a smooth polished texture which minimizes the possibility that bacteria could be trapped thereabouts. Preferably, the smooth coronal surface 42 extends in the axial direction a distance of approximately 2 to 4 mm. The distalmost three-quarters of the implant body 12 which functions as a bone engaging surface is provided with the porous coated surface 40 formed by spray coating the implant with titanium beads. The porous surface 40 of the bone-engaging region of the implant body 12 may be in the form of a coating comprised of discrete titanium beads or particles adhered to a remainder of the implant body 12 into which the patient's bone tissues 20 and/or 22 may grow. Other porous coatings and/or constructs may also be used including porous coatings formed by mechanical abrasion, or a roughened portion of the implant. Preferably, the porous surface 40 is formed having a porosity of from about 10 to 800 microns, with the porous coated surface having a porosity similar to that of the Endopore® implants. Differing porosities are, however, also possible.

Figure 4:
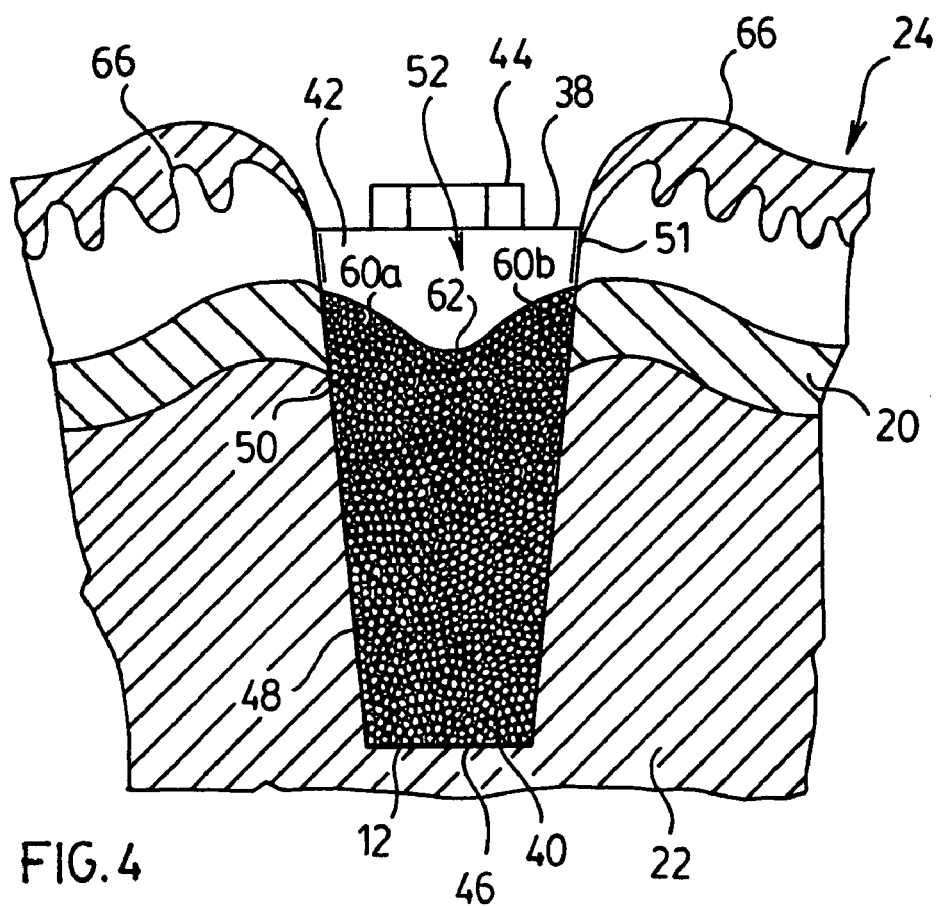
FIG. 4 shows a schematic side view of the lingual surface of the implant body of FIG. 2 seated within a patient's jaw bone.

As shown best in FIGS. 2 and 4, the porous coated surface 40 is characterized by two axially elongated and proximally extending regions 60a,60b which extend on each of the opposing distal and mesial sides 50,51 of the implant body 12. In each of the regions 60a,60b, the porous coated surface 40 extends an increased distance from the distal apex 46 of the implant body 12 towards its proximal end surface 38 relative to the portions of the porous coated surface 40 along the lingual and buccal implant sides 52,54. More preferably, the regions 60a,60b extend approximately 2 to 4 mm closer to the end surface 38 of the implant body 12 than the coated surface 40 at the buccal and lingual surfaces 52,54. As seen best in FIG. 2, in this manner the upper edge 62 of the porous coated surface 40 which is spaced closest to the implant body end 38 rides upwardly into the collar 42 along both the distal and mesial sides 50,51 of the implant 10. Most preferably, the proximal-most edge 62 of the porous surface 40 is formed so as to follow a predetermined profile, as for example the profile of the crestal ridge of typical healthy bone tissue 20 and/or alveolar tissues 22 at the site of intended implant use.

It is to be appreciated that providing the proximal edge 62 of the porous coated portion 40 of the implant body 12 with a profile which generally follows the profile of healthy bone tissue advantageously stimulates bone tissues to engage the dental implant body 12 in the identical manner that occurs with natural teeth. As such, sites of higher bone tissue 20,22 engagement occur along the mesial and distal side portions 51,50 of the implant body 12. It is to be appreciated that the sites of higher bone tissue 20,22 engagement in turn maintain the shape and crestal outline of interdental bone and overlying gum tissues 66 (FIG. 4) at the optimum spacing from the cementoenamel junction of the tooth, eliminating "black triangles" between implants 10 and adjacent natural teeth. In addition, the higher sites of bone tissue 20,22 attachment reduce the likelihood of alveolar bone tissue 22 loss which may otherwise result in the exposure of the collar 42 of the implant body 12.

To ensure proper orientation of the implant body 12 seated within the bore 48, the proximal surface 38 of the body 12 may further include visual indicia 68 (see stamped letters D and M) or other striations, grooves, guides or posts used to assist in orienting the implant body 12 following its placement in the patient's jaw 24.

Figure 5:
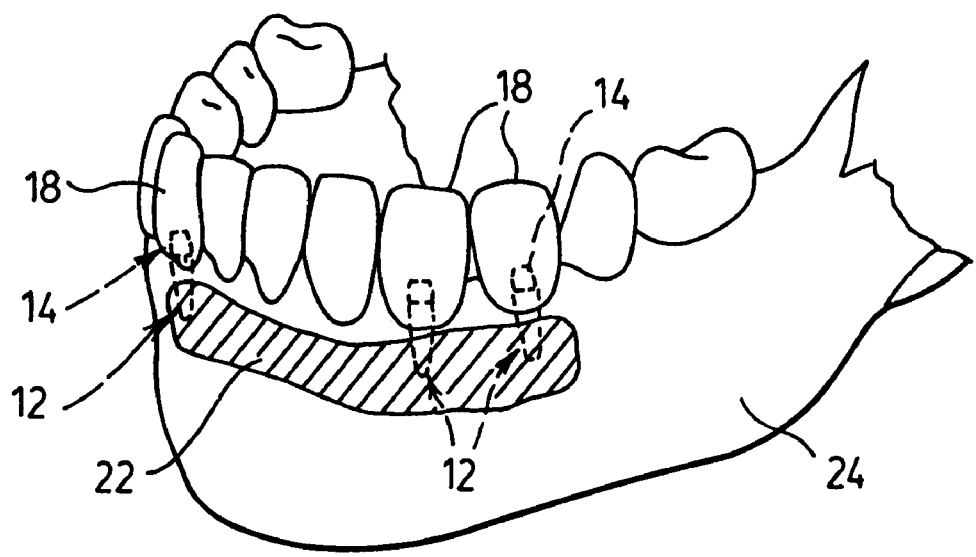
FIG. 5 shows a schematic view of the implant construction shown in FIG. 1 seated in place within a patient's jaw bone.

In installation of the implant 10, a frustoconical shaped bore 48 is formed in the patient's jaw 24 at the site of intended tooth replacement, as for example is shown in FIG. 5. The bore 48 is formed to a depth selected so that the cementoenamel junction of the prosthesis 18 and collar 42 locates at a position corresponding to that of a natural healthy tooth. The implant body 12 is then inserted in the bore 48 in a press fit arrangement and the indicia 68 is used to facilitate in orienting the implant body 12 so that the distal and mesial sides 50,51 assume the desired orientation in the patient's jaw bone. Following placement of the implant, a temporary cap (not shown) is secured over the hexagonal mount 44 and proximal end 38 and the implant body 12 is sutured over and allowed to heal for several weeks.

After a passage of time which is selected to permit the bone tissue 20,22 ingrowth into the bone engaging porous coated surface 40, so as to sufficiently anchor the implant body, the temporary cap is removed. The abutment assembly 14 is then secured to the implant body 12 by means of the threaded engagement of the screw 16 within the bore 36. The prosthesis 18 is thereafter positioned over and affixed over the abutment 14 by a suitable dental cement.

The implant body 12 is constructed such that it may be placed in a press-fit manner with the raised regions 60a,60b of the porous portions 40 oriented in a distal/mesial alignment, and the buccal and lingual sides 54,52 of the positioned implant body 10 characterized by the porous coated regions of a comparably shorter length. In an optimum construction, the implant body 12 is constructed such that:

The proximal edge 62 of the porous coating 40 is curved or follows a contour whereby the buccal/lingual side portions 54,52 are more apical relative to the mesial/distal side portions 50,51 by 2 to 4 mm.
The implant body 12 is adapted to be "press fitted" in the patient's jaw.
The smooth collar 42 of the body 12 is at least 1.5–2 mm wide.
The implant can be offered in the same diameters and lengths as the Endopore® implants.

Although FIGS. 1 to 4 illustrates the implant body 12 as having a bone engaging porous coated surface 40 which includes elongated regions 60a,60b extending towards the proximal end surface 38 and into the collar 42 along the distal and mesial sides 50,51 of the positioned implant 10, the invention is not so limited. It is to be appreciated that in an alternate configuration, the proximal edge 62 of bone engaging porous surface 40 of the implant body 12 could include only one elongated porous coated region extending into the collar 42 along only one of the distal side 50 or mesial side 52 of the implant. In an alternate construction, the porous surface 40 could have elongated regions extending proximally along the lingual and/or buccal sides 52,54 of the implant body 12.

Although FIGS. 1 to 4 illustrate the implant body 12 as having a generally flat proximal end surface 38, the invention is not so limited. Reference may be had to FIG. 6 which shows an alternate implant body construction in which like reference numerals are used to identify like components. In FIG. 6, the proximal end 38 of the implant body 12 is contoured so as to generally follow the same contour as the proximal edge 62 of the bone engaging porous surface 40. It is to be appreciated that with the contoured proximal end surface 38, a modified abutment assembly is provided which is adapted to substantially mate with the contoured end 38 in assembly of the implant 10. In the construction shown, the non-porous coronal surface 42 follows the uppermost edge 62 of the porous coated surface 40 as a smooth band having a substantially constant width, which most preferably is selected at about 1.5 to 2.5 mm in width. It is to be appreciated, however, that a coronal surface 42 could also be provided which narrows in width at each raised region 60a,60b of the porous surface 40.

Although FIGS. 1 to 5 illustrate the implant 10 as having a tapered implant body 12, the invention is not so limited. It is to be appreciated that the present invention is also operable with an implant body 12 which, for example, could be parallel sided or for that matter which could include a combination of parallel sided and tapered portions, without departing from the spirit and scope of the present invention.

Reference is made to FIG. 7 which illustrates a further embodiment of the invention wherein like reference numerals are used to identify like components. In FIG. 7, the dental implant body 12 is cylindrical in shape. The body 12 includes a distalmost bone engaging portion 140 which is provided with external helical threads 80 as the means by which bone engagement and anchorage of the implant body 12 is achieved. As with the porous coating 40 of the implant body 12 shown in FIG. 1, the helical threads 80 of the implant body 12 of FIG. 5 extend from a distalmost apex 40 upwardly to a proximal-most edge 62. The external threads 80 extend axially in the proximal direction further along the distal side (50) and mesial side (not shown) of the implant body 12 than the regions of the external threads in the lingual and buccal 52,54 side portions. As with the raised porous region 60a,60b, the elongated threaded region 60a shown in FIG. 5 thus extends closer to the proximal end surface 38 of the implant body and further proximally into the smooth collar 42 than the threads 80 of the implant body 12 along its lingual and buccal sides 52,54.

In FIG. 7, the implant body 12 is similarly provided with a hexagonal or other polygonally shaped mount 44. In addition to serving as a mount for the abutment assembly 14, the mount 44 advantageously may be used to assist in theaddly inserting the implant body 12 into the patient's jaw bone. If desired, the external hexagonal mount 50 on the implant body 12 could be provided with grooves, slots or other visual indicia which facilitate the positioning of the implant body 12 so that the elongated threaded regions 60 are in alignment with the mesial and distal surfaces of the patient's immediately adjacent teeth.

FIG. 8 illustrates a further embodiment of the invention in which like reference numerals are used to identify like components. In FIG. 8, the implant body 12 includes a conventional externally threaded bone engaging portion 140. In the embodiment as shown, the implant body 12 further includes an enlarged flared non-porous upper portion 142. A threaded bore (not shown) is formed in the proximal end surface 38 of the implant body 12 and is adapted for the mechanical coupling of an abutment assembly and prosthesis (not shown) thereto in a conventional manner. To provide an enhanced bone engaging surface, a bioreactive coating 144 is provided over the externally threaded portion 140 and part of upper portion 142 of the implant body 12. The coating 144 extends further towards the proximal surface 38 along the lingual side 52 and buccal side 54 of the implant body as regions 160a, 160b. It is to be appreciated, however, that the coating 144 could equally extend further along the mesial and/or distal sides of the implant in the similar manner as the porous coated surface 40 shown in FIG. 1. The bioreactive coating 144 which is selected to facilitate the engagement of bone tissues with the implant and suitable coatings include without restriction, hydroxyapatite coatings and the like. As with the embodiments shown in FIGS. 1 to 5, the proximal-most edge 162 of the bioreactive coating 144 has a contour which is selected to follow a predetermined contour, as for example, which follows the profile of the crestal surface of either a healthy jaw bone or the patient's own jaw bone.

FIG. 9 illustrates another embodiment of the invention in which like reference numerals are used to identify like components. In FIG. 9, the implant body 12 tapers from the distal apex end 46 of the implant body to the proximal end 38. As with the implant construction shown in FIG. 6, the proximal end 38 is provided with a contoured profile, which generally follows the same contour as the proximal edge 62 of the bone engaging porous coated surface 40, and the crestal surface contour.

As with the implant shown in FIGS. 1 to 4, the porous surface 40 most preferably is formed by a coating of discreet titanium of ceramic beads or particles which are adhered to the remainder of the implant body. The porous coating is selected to form a porosity of from between about 10 to 800 microns. Other manner of forming the porous coating including mechanical abrasion and/or roughening are however also envisioned as possible.

The implant body 12 of FIG. 9 includes a textured transition zone 104 which is provided between the porous coated portion 40 of the implant body 12, and the smooth coronal surface 42. The transition zone 102 is characterized by a roughened textured surface which, for example, is preferably formed by laser abradement, acid etching and/or other mechanical abradement.

The transitional band 102 is provided as a contoured band extending in the direction of axis $A-A_1$ between about 0.25 to 3 mm, preferably between about 0.5 and 2.5 mm, and more preferably from about 0.75 to about 1.5 mm. In a simplified construction, the transitional band 102 has a substantially constant width and mimics the path of the crestal surface contour. It is to be appreciated, however, that the band 102 could be provided so as to narrow or increase in width at each of the raised and/or lower regions on the porous surface 40 without departing in scope from the present invention.

The coronal surface 42 is formed as non-porous coloured substantially smooth coated or plated band 104. The coloured coronal band 104 preferably extends from the proximal end 38 of the implant body 12 to a lower edge 108 spaced distally towards the apex end 46. The coloured coronal band 104 has a width in the direction of axis $A-A_1$ of between about 0.5 and 2.5 mm, and more preferably about 0.75 to 1.25 mm. Although not essential, the lower edge 108 of the band 104 preferably generally follows the contour of the proximal edge 62 surface of the porous surface 40.

It has been found that with conventional silver stainless steel and titanium implants, when a patient experiences partial recession of supporting gum tissue, the silver/grey colour of conventional titanium or stainless steel implants shows through the translucent gum tissues, tinting the gum tissues a grayish colour. The silver/grey colouring presents an unnatural and aesthetically displeasing appearance to the patient. To overcome these disadvantages, the coloured band 104 is provided with colour which is more complementary to the patient's gum tissue colour, and which is selected so that when shown through translucent gum tissue, the band colour does not significantly tint the gum tissue from its natural colour. More preferably, the coloured band 104 is provided with a yellow gold or pink gold colouring. In such a construction, the coloured coronal band portion is formed by applying a gold coloured titanium nitride plating or coating, a, yellow gold or gold alloy coating or plating, or a pink gold or gold alloy plating or coating to the implant body 12 to form the smooth band 104. Other alloys used to create suitable coloured platings and coatings will also now become apparent.

Although FIG. 9 illustrates the coloured coronal band of the implant body 12 as extending to a contoured lower edge 108, the invention is not so limited. It is to be appreciated that the coloured band could be provided along the non-contoured proximal edge 38 of each of the implant bodies shown in FIGS. 1, 5, 7 or 8 and which extends the lower edge which is either parallel to the contoured edge 38 or the proximal edge 62 of the bone engaging portion.

While it may be preferred that the implant body 12 include two opposed elongated coated regions 160a, 160b on both the distal/mesial sides 50,51 of the implant body 12, the invention is not so limited. If desired, the body 12 could be modified to include only a single elongated coated region 160a where for example, the implant 10 is to be placed in a position interposed between a natural tooth and a second implant. In this construction, any proximally extending or elongated portion of the coating 144 would be located adjacent to the second implant alone. Alternately, it is envisioned that the implant having two or more non-opposed discrete elongated coated regions 160a, 160b could be provided for specific orientation, where the loss of supporting bone height may otherwise occur.

Although FIGS. 1 to 4 illustrate the implant body 12 as including a hexagonal mount or projection 44 sized for complementary insertion within the bore 46 of the abutment assembly 14, the invention is not so limited. Other forms and configurations of mounts may also be used and will now become apparent. In a less preferred embodiment, the mount may be omitted in its entirety or alternately, a complementary form recess could be provided within the implant body 12. The hexagonal projection 44, however, is believed to represent a preferred construction in that it acts to correctly seat the abutment 14, preventing any rotational movement thereof once secured against the implant body surface 38. The hexagonal projection 44 most preferably is of a standard size so as to provide compatibility with a variety of prosthetic systems from a variety of different manufacturers.

Although FIG. 1 illustrates the abutment assembly 14 as comprising a single piece, the invention is not so limited. It is to be appreciated that the present invention is suitable for use with a variety of abutment configurations including, without restriction, other single, two-piece and multiple-piece abutments.

Although the preferred embodiments of the invention disclose and describe the bone engaging regions of the implant body 12 as comprising a porous coated surface, an externally threaded surface or a biochemically coated surface, the invention is not so limited. It is to be appreciated that other bone engaging surfaces could also be used with the present invention, including, without restriction, the use of other textured or roughened surfaces which are provided with a contoured profile selected to follow the crestal surface of a patient's or other preselected jaw bone tissues.

Although the preferred embodiment of the invention describes and illustrates various preferred aspects of the invention, the invention is not so limited. Many modifications and variations will now occur to persons skilled in the art. For a definition of the invention, reference may be had to the appended claims.

We claim:

1. A dental implant for use in replacing a missing tooth in a patient's jaw bone comprising, an implant body adapted to be at least partially recessed into a portion of said patient's jaw bone, said implant body extending longitudinally along an axis from a distalmost apex to a proximal end portion,
   a colored coronal band portion provided about a peripheral surface of said implant body adjacent said proximal end portion, said colored portion having a color which is complementary to a natural gum tissue color of said patient, so as not to significantly discolor the gum tissue if seen therethrough,
   a bone engaging surface provided about at least a portion of said peripheral surface of said implant body, and being spaced from said colored band portion towards said apex said bone engaging surface selected to promote bone tissue ingrowth or attachment thereto and extending longitudinally along said periphery of said implant body to a proximal edge spaced towards said proximal end portion, wherein at least a portion of said proximal edge having a contour selected to generally follow a crestal surface contour of preselected bone tissues.

2. An implant as claimed in claim 1 wherein said coloured band portion extends from said proximal end portion towards said apex a distance selected at between about 0.5 and 2.5 mm.

3. An implant as claimed in claim 2 wherein said bone engaging surface is selected from the group consisting of a porous coated surface, a textured surface, an externally threaded surface and a biochemically coated surface.

4. An implant as claimed in claim 3 wherein said proximal end portion is contoured so as to generally follow said crestal surface contour, and said implant body is sized for insertion in an anterior region of said patient's mouth.

5. An implant as claimed in claim 1 wherein said implant body includes a generally cylindrical portion, said bone engaging surface extending about a periphery of at least part of said cylindrical portion.

6. An implant as claimed in claim 5 wherein said implant body is generally frustoconical in shape, said body tapering from said proximal end portion towards said apex at an angle of between 1 and 20 degrees.

7. An implant as claimed in claim 6 wherein said implant body tapers at an angle of about 5 degrees.

8. An implant as claimed in claim 1 wherein said implant body includes a tapered portion, said tapered portion narrowing in diameter towards said apex at an angle of between about 1 and 20 degrees, and said colored band portion comprises a coating selected from the group consisting of a gold colored titanium nitride coating, a yellow gold or gold alloy coating and a pink gold or gold alloy coating.

9. An implant as claimed in claim 8 wherein said implant body further comprises orienting means to assist in orienting said implant body with the contour of the proximal edge substantially aligned with the contour of the crestal surface of said patient's jaw bone, said orienting means selected from the group consisting of visual indicia, grooves, stamped markings, and guide members.

10. A dental implant as claimed in claim 2 wherein said implant body includes a textured peripheral portion intermediate said bone engaging surface and said colored band portion, said textured peripheral portion selected from a laser abraded surface, an acid etched surface and a mechanically abraded or roughened surface.

11. A dental implant for use in replacing a missing tooth in a patient's jaw bone comprising,
    an implant body portion adapted to be recessed into a portion of said patient's jaw bone, said implant body extending longitudinally along an axis from a distalmost apex to a proximal end portion,
    a colored coronal band portion provided about said implant body portion immediately adjacent said proximal end portion, said colored band portion comprising a gold colored plating or coating and extending axially between 0.5 to 2.5 mm along said implant body,
    a bone engaging surface spaced distally from said colored band coating towards said apex and providing a peripheral surface of said implant body, said bone engaging surface selected to promote bone tissue ingrowth or attachment thereto and extending longitudinally along said periphery of said implant body to a proximal edge spaced towards said proximal end portion, wherein the proximal edge of the bone engaging surface has a contour selected to generally follow a crestal surface contour of a pre-selected jaw bone adjacent said missing tooth.

12. An implant as claimed in claim 11 further comprising a textured implant surface extending about a periphery of said implant body intermediate said bone engaging surface and said colored band surface, said bone engaging surface comprising a porous surface, said textured surface being selected from a chemically etched, a laser abraded and mechanically abraded surface and wherein said colored band portion is selected from a titanium nitride coated portion and a gold or gold alloy coated portion.

13. An implant as claimed in claim 11 wherein said porous surface has a porosity selected at between about 20 and 800 microns.

14. The implant as claimed in claim 12 wherein the proximal end portion is contoured to generally follow said crestal surface contour, and
    said coloured band portion extends distally from said proximal end portion to a lower band edge, said lower band edge.

15. The implant of claim 14 wherein said lower band edge generally follows the contour of the proximal edge of the bone engaging surface, and said textured surface extends in the axial direction a distance of between about 0.5 and 2.5 mm.

16. An implant as claimed in claim 11 wherein said bone engaging surface comprises an externally threaded surface.

17. An implant as claimed in claim 11 wherein said bone engaging surface comprises a biochemically coated surface, selected from a hydroxyapatite coating and a calcium hydroxyapatite coating.

18. An implant as claimed in claim 11 wherein said coloured band portion comprises a generally smooth portion.

19. An implant as claimed in claim 18 wherein said bone engaging surface is selected from the group consisting of a porous surface, a textured surface, a threaded surface and a biochemically coated surface.

20. An implant as claimed in claim 11 wherein said pre-selected jaw bone comprises the jaw bone of a healthy human.

21. An implant as claimed in claim 11 wherein said pre-selected jaw bone comprises the jaw bone of said patient.

22. A dental implant for use in replacing a natural tooth in a patient's jaw bone comprising, an implant body extending longitudinally along an axis from a lowermost apex to an upper end portion and including, an uppermost colored coronal band surface adjacent to said upper end portion and providing a first peripheral surface portion of said implant body said colored band portion comprising a substantially smooth portion having applied thereto a coating selected from a group consisting of a gold colored titanium nitride coating, a yellow gold coating, a yellow gold alloy coating, a pink gold coating, and a pink gold alloy coating, a bone engaging surface providing a second peripheral surface portion of said implant body adapted to be recessed into said patient's jaw bone, said bone engaging surface selected to promote bone tissue ingrowth or attachment thereto and extending longitudinally along said periphery of said implant body substantially from said apex to an upper edge spaced towards said upper end portion, wherein the upper edge of the bone engaging surface has a contour selected to generally follow a crestal surface contour of healthy bone tissues at a site of implant placement, and a textured peripheral portion intermediate said bone engaging surface and said colored band portion, the textured peripheral portion selected from a laser abraded portion, an acid etched portion, and mechanically abraded portion, and an abutment for supporting a prosthesis thereon.

23. The implant as claimed in claim 22 wherein said implant body is generally frustoconical in shape tapering inwardly towards said apex at an angle of between about 2 and 10 degrees, and said bone engaging surface comprises a porous coated surface.

* * * * *